US00PP19481P2

(12) United States Plant Patent
Klemm

(10) Patent No.: US PP19,481 P2
(45) Date of Patent: Nov. 25, 2008

(54) ***GERANIUM* PLANT NAMED 'KLEPP06124'**

(50) Latin Name: *Pelargonium peltatum*
Varietal Denomination: KLEPP06124

(75) Inventor: Nils Klemm, Stuttgart (DE)

(73) Assignee: Klemm + Sohn + GmbH + Co. KG, Stuttgart (DE)

( * ) Notice: Subject to any disclaimer, the term of this patent is extended or adjusted under 35 U.S.C. 154(b) by 0 days.

(21) Appl. No.: 12/002,457

(22) Filed: Dec. 17, 2007

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

UPOV ROM GTITM Computer Database, GTI Jouve Retrieval Software May 2007 Citation for 'KLEPP06124'.*

* cited by examiner

*Primary Examiner*—Wendy C. Haas
(74) *Attorney, Agent, or Firm*—C. A. Whealy

(57) ABSTRACT

A new and distinct cultivar of Ivy *Geranium* plant named 'KLEPP06124', characterized by its compact, outwardly spreading to trailing plant habit; freely branching habit; freely and early flowering habit; semi-double red purple-colored flowers; and good garden performance.

1 Drawing Sheet

Botanical designation: *Pelargonium peltatum.*
Cultivar denomination: 'KLEPP06124'.

BACKGROUND OF THE INVENTION

The present invention relates to a new and distinct cultivar of Ivy *Geranium*, botanically known as *Pelargonium peltatum,* and hereinafter referred to by the name 'KLEPP06124'.

The new Ivy *Geranium* is a product of a planned breeding program conducted by the Inventor in Stuttgart, Germany. The objective of the breeding program is to create new freely-branching and uniform Ivy *Geranium* cultivars with early flowering habit and attractive foliage and flower coloration.

The new Ivy *Geranium* originated from a cross-pollination made by the Inventor in Stuttgart, Germany in July, 2002 of a proprietary selection of *Pelargonium peltatum* identified as code number P 20 028, not patented, as the female, or seed, parent with the *Pelargonium peltatum* cultivar Royal White, not patented, as the male, or pollen, parent. The cultivar KLEPP06124 was discovered and selected by the Inventors as a flowering plant from within the progeny of the stated cross-pollination in a controlled environment in Stuttgart, Germany in June, 2003.

Asexual reproduction of the new Ivy *Geranium* by vegetative terminal cuttings in a controlled environment in Stuttgart, Germany since September, 2003, has shown that the unique features of this new Ivy Geranium are stable and reproduced true to type in successive generations.

SUMMARY OF THE INVENTION

The cultivar KLEPP06124 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'KLEPP06124'. These characteristics in combination distinguish 'KLEPP06124' as a new and distinct cultivar of Ivy *Geranium:*

1. Compact, outwardly spreading to trailing plant habit.
2. Freely branching habit.
3. Freely and early flowering habit.
4. Semi-double red purple-colored flowers.
5. Good garden performance.

Plants of the new Ivy *Geranium* differ primarily from plants of the female parent selection in the following characteristics:

1. Plants of the new *Geranium* are more compact than and not as vigorous as plants of the female parent selection.
2. Plants of the new *Geranium* and the female parent selection differ in flower color as plants.

Plants of the new Ivy *Geranium* differ primarily from plants of the male parent, the cultivar Royal White, primarily in flower color as plants of the cultivar Royal White have white-colored flowers.

Plants of the new Ivy *Geranium* can be compared to plants of the *Pelargonium peltatum* cultivar Royal Magenta, not patented. In side-by-side comparisons conducted in Stuttgart, Germany, plants of the new Ivy *Geranium* differed from plants of the cultivar Royal Magenta in the following characteristics:

1. Plants of the new Ivy *Geranium* were more compact than plants of the cultivar Royal Magenta.
2. Plants of the new Ivy *Geranium* and the cultivar Royal Magenta differed in flower color as plants of the cultivar Royal Magenta had purple magenta-colored flowers.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph is a close-up view of typical flowers and leaves of 'KLEPP06124'.

DETAILED BOTANICAL DESCRIPTION

The aforementioned photographs and following observations, measurements and values describe plants grown in Stuttgart, Germany in 12-cm containers in a glass-covered greenhouse during the spring and under conditions which closely approximate commercial *Geranium* production. During the production of the plants, day temperatures ranged from 16° C. to 23° C., night temperatures ranged from 8° C. to 16° C. and light levels ranged from 20,000 lux to 50,000 lux. Plants were about three months old when the photograph and the description were taken. In the detailed description, color references are made to The Royal Horticultural Society Colour Chart, 2001 Edition, except where general terms of ordinary dictionary significance are used.

Botanical classification: *Pelargonium peltatum* cultivar KLEPP06124.

Parentage:

*Female, or seed, parent.*—Proprietary selection of *Pelargonium peltatum* identified as code number P 20 028, not patented.

*Male or pollen parent.*—*Pelargonium peltatum* cultivar Royal White, not patented.

Propagation:

*Type.*—By vegetative terminal cuttings.

*Time to initiate roots, summer.*—About five days at temperatures of 22° C.

*Time to initiate roots, winter.*—About six days at temperatures of 20° C.

*Time to produce a rooted young plant, summer.*—About 16 days at temperatures of 22° C.

*Time to produce a rooted young plant, winter.*—About 20 days at temperatures of 18° C.

*Root description.*—Medium in thickness, fibrous; white in color.

*Rooting habit.*—Freely branching, moderately dense.

Plant description:

*Plant/growth habit.*—Compact outwardly spreading to trailing plant habit, mounding; densely foliaged. Moderately vigorous growth habit. Freely basal branching habit with about four lateral branches per plant.

*Plant height, to top umbels.*—About 20 cm to 24 cm.

*Plant height, to top of leaves.*—About 12 cm to 18 cm.

*Plant width.*—About 18 cm to 22 cm.

*Lateral branches.*—Length: About 5 cm to 6 cm. Internode length: About 0.6 cm to 1 cm. Texture: Pubescent. Color: 137A.

Foliage description:

*Arrangement.*—Alternate; simple.

*Length.*—About 5 cm to 6 cm.

*Width.*—About 7 cm to 8 cm.

*Shape.*—Reniform.

*Apex.*—Obtuse.

*Base.*—Cordate.

*Margin.*—Entire.

*Venation pattern.*—Palmate.

*Texture, upper and lower surfaces.*—Glabrous, leathery.

*Color.*—Developing and fully expanded foliage, upper surface: 137A; venation, 137B. Developing and fully expanded foliage, lower surface: 137B; venation, 137C. Zonation pattern: Distance from leaf margin: About 1 cm. Width: About 0.8 mm. Color: 177A. Petiole: Length: About 3 cm to 5 cm. Diameter: About 3 mm. Texture, upper and lower surfaces: Rough. Color, upper and lower surfaces: 137B.

Flower description:

*Flower arrangement.*—Semi-double rotated flowers arranged in rounded hemispherical umbels arising from apical leaf axils. Umbels displayed above the foliage on strong peduncles. Flowers face upright to outward; flowers slightly cupped. Flowers not persistent. Flowers not fragrant.

*Quantity of flowers.*—Freely flowering habit; about 12 to 18 flower buds and open flowers per umbel; about seven to nine umbels per plant.

*Flowering season.*—Year-round under greenhouse conditions. In the garden in Stuttgart, Germany, flowering is continuous from spring until frost in autumn.

*Flower longevity.*—Individual flowers last about four to five days on the plant.

*Umbel height.*—About 8 cm.

*Umbel diameter.*—About 6 cm to 8 cm.

*Flower diameter.*—About 4 cm.

*Flower depth (height).*—About 1 cm to 2 cm.

*Flower buds.*—Length: About 1 cm to 1.4 cm. Diameter: About 5 mm to 8 mm. Shape: Elliptic. Color: 137B.

*Petals.*—Quantity per flower: About eight to twelve. Length: About 2.5 cm. Width: About 1.2 cm. Shape: Ovate. Apex: Rounded. Base: Attenuate. Margin: Entire. Texture, upper and lower surfaces: Smooth, glabrous; velvety. Color: When opening, upper surface: 74B. When opening, lower surface: 65C. Fully opened, upper surface: 74D; towards the base, 65D; venation, 74A. Fully opened, lower surface: 65C; towards the base, 65D; venation, 74B.

*Petaloids.*—Quantity per flower: None to about five. Length: About 3 mm to 10 mm. Width: About 2 mm to 5 mm. Shape: Irregularly-shaped. Apex: Rounded. Base: Attenuate. Margin: Entire. Texture, upper and lower surfaces: Smooth, glabrous; velvety. Color: When opening, upper surface: 74B. When opening, lower surface: 65C. Fully opened, upper surface: 74D; towards the base, 65D; venation, 74C. Fully opened, lower surface: 65C; towards the base, 65D; venation, 74D.

*Sepals.*—Quantity per flower: Five, arranged in a single whorl. Length: About 6 mm to 9 mm. Width: About 4 mm to 6 mm. Shape: Elliptic. Apex: Acute. Base: Attenuate. Margin: Entire. Texture, upper surface: Smooth. Texture, lower surface: Rough. Color, upper and lower surfaces: 137B.

*Peduncle (umbel stem).*—Length: About 10 cm to 15 cm. Diameter: About 6 mm. Strength: Strong. Angle: Mostly erect. Texture: Slightly pubescent. Color: 137A.

*Pedicel (individual flower stem).*—Length: About 2 cm to 2.5 cm. Diameter: About 2 mm. Strength: Moderately strong. Angle: Erect to about 110° C. from vertical. Texture: Slightly pubescent. Color: 137B overlain with 173A.

*Reproductive organs.*—Androecium: Stamen quantity per flower: About five. Anther length: About 3 mm.

Anther shape: Ovate. Anther color: 49A. Pollen amount: Moderate. Pollen color: 33A. Gynoecium: Pistil quantity per flower: One. Pistil length: About 8 mm to 10 mm. Stigma shape: Tapering; reflexed. Stigma color: 57C. Style length: About 3 mm to 5 mm. Style color: 57D. Ovary color: 149D.

*Seed.*—Seed development has not been observed.

Disease/pest resistance: Plants of the new Ivy *Geranium* have not been observed to be resistant to pathogens and pests common to Ivy *Geraniums.*

Garden performance: Plants of the new Ivy *Geranium* have been observed to tolerate rain, wind and temperatures ranging from about 8° C. to about 31° C. and have demonstrated good garden performance.

It is claimed:

1. A new and distinct Ivy *Geranium* plant named 'KLEPP06124' as illustrated and described.

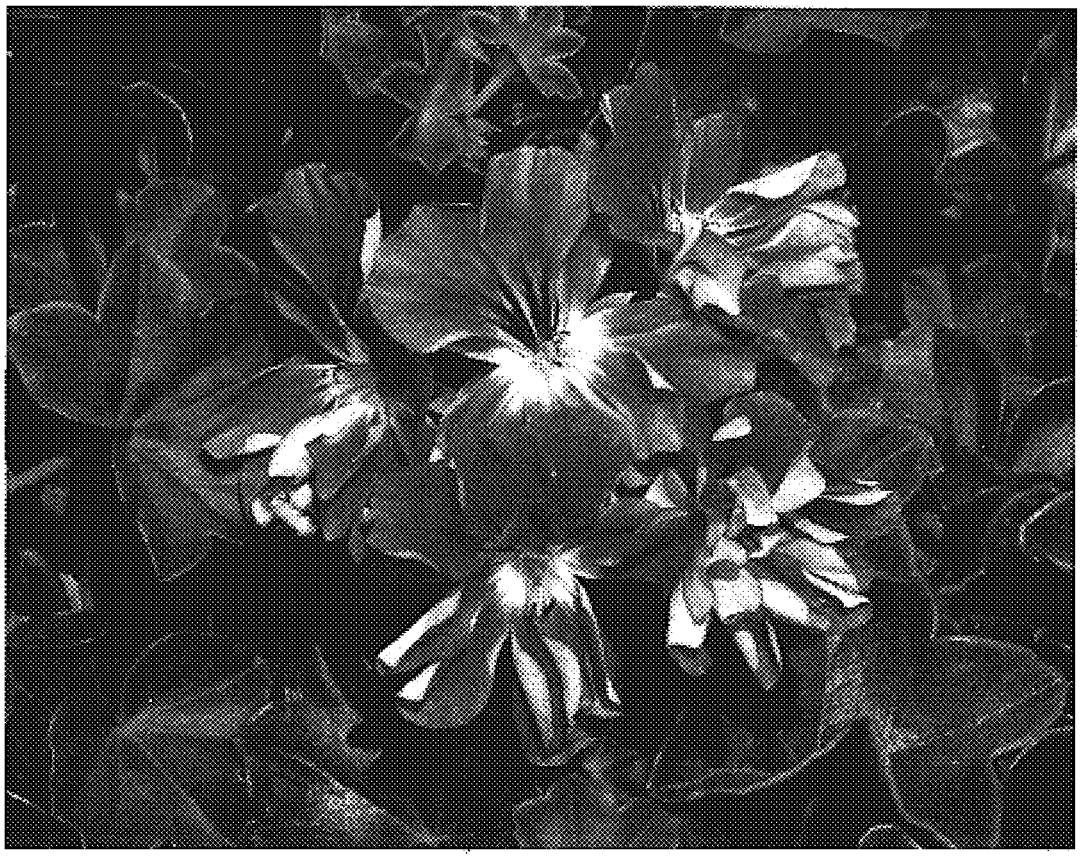

* * * * *